United States Patent
Grossman

(10) Patent No.: US 9,357,977 B2
(45) Date of Patent: Jun. 7, 2016

(54) INTERVENTIONAL DEPLOYMENT AND IMAGING SYSTEM

(75) Inventor: Jessica Grossman, San Francisco, CA (US)

(73) Assignee: Gynesonics, Inc., Redwood City, CA (US)

(*) Notice: Subject to any disclaimer, the term of this patent is extended or adjusted under 35 U.S.C. 154(b) by 1460 days.

(21) Appl. No.: 11/620,594

(22) Filed: Jan. 5, 2007

(65) Prior Publication Data

US 2007/0179380 A1    Aug. 2, 2007

Related U.S. Application Data

(60) Provisional application No. 60/758,881, filed on Jan. 12, 2006.

(51) Int. Cl.

| | |
|---|---|
| *A61B 5/05* | (2006.01) |
| *A61B 8/08* | (2006.01) |
| *A61B 8/12* | (2006.01) |
| *A61B 8/14* | (2006.01) |
| *A61B 18/14* | (2006.01) |
| *A61B 1/303* | (2006.01) |
| *A61B 5/00* | (2006.01) |

(Continued)

(52) U.S. Cl.
CPC .......... *A61B 8/0833* (2013.01); *A61B 5/0073* (2013.01); *A61B 5/412* (2013.01); *A61B 5/6852* (2013.01); *A61B 8/0841* (2013.01); *A61B 8/12* (2013.01); *A61B 8/14* (2013.01); *A61B 18/1477* (2013.01); *A61B 1/303* (2013.01); *A61B 5/0066* (2013.01); *A61B 2017/4216* (2013.01); *A61B 2018/00559* (2013.01); *A61B 2018/1475* (2013.01); *A61B 2218/002* (2013.01)

(58) Field of Classification Search
USPC ......... 600/407, 425–427, 436, 437, 439–447, 600/459–466, 470, 471, 472, 476, 478
See application file for complete search history.

(56) References Cited

U.S. PATENT DOCUMENTS

| | | | |
|---|---|---|---|
| 4,289,132 A | 9/1981 | Rieman | |
| 4,936,281 A | 6/1990 | Stasz | |
| 5,335,663 A * | 8/1994 | Oakley et al. ................ | 600/463 |

(Continued)

FOREIGN PATENT DOCUMENTS

| | | |
|---|---|---|
| WO | WO 97/17105 | 5/1997 |
| WO | WO 98/11834 | 3/1998 |

(Continued)

OTHER PUBLICATIONS

International Search Report and Written Opinion of PCT Application No. PCT/US07/60306, dated Mar. 3, 2008.

(Continued)

*Primary Examiner* — Mark Remaly
(74) *Attorney, Agent, or Firm* — Wilson, Sonsini, Goodrich & Rosati

(57) ABSTRACT

Needle deployment and imaging system includes a sheath, an imaging core, and interventional core. The imaging core and interventional core are received in first and second axial passages in the sheath and at least one of said cores will be removable and replaceable within the sheath. The imaging core may be extended from the sheath or be sealed within the first axial passage of the sheath. The interventional core will typically be advanced laterally or axially from a location near the distal end of the sheath.

25 Claims, 6 Drawing Sheets

(51) Int. Cl.
*A61B 17/42* (2006.01)
*A61B 18/00* (2006.01)

(56) References Cited

U.S. PATENT DOCUMENTS

| | | | |
|---|---|---|---|
| 5,372,587 A | 12/1994 | Hammerslag et al. |
| 5,456,689 A | 10/1995 | Kresch |
| 5,469,853 A | 11/1995 | Law et al. |
| 5,471,988 A | 12/1995 | Fujio et al. |
| 5,492,126 A | 2/1996 | Hennige et al. |
| 5,527,331 A | 6/1996 | Kresch et al. |
| 5,531,676 A | 7/1996 | Edwards et al. |
| 5,649,911 A | 7/1997 | Trerotola |
| 5,666,954 A | 9/1997 | Chapelon et al. |
| 5,697,897 A | 12/1997 | Buchholtz et al. |
| 5,730,752 A | 3/1998 | Alden et al. |
| 5,741,287 A | 4/1998 | Alden et al. |
| 5,752,518 A | 5/1998 | McGee et al. |
| 5,769,880 A | 6/1998 | Truckai et al. |
| 5,860,974 A | 1/1999 | Abele |
| 5,863,294 A | 1/1999 | Alden |
| 5,873,828 A | 2/1999 | Fujio et al. |
| 5,876,340 A | 3/1999 | Tu et al. |
| 5,876,399 A | 3/1999 | Chia et al. |
| 5,891,137 A | 4/1999 | Chia et al. |
| 5,906,615 A | 5/1999 | Thompson |
| 5,916,198 A | 6/1999 | Dillow |
| 5,957,941 A | 9/1999 | Ream |
| 5,979,452 A | 11/1999 | Fogarty et al. |
| 5,979,453 A | 11/1999 | Savage et al. |
| 5,984,942 A | 11/1999 | Alden et al. |
| 6,002,968 A | 12/1999 | Edwards |
| 6,007,499 A | 12/1999 | Martin et al. |
| 6,032,673 A | 3/2000 | Savage et al. |
| 6,039,748 A | 3/2000 | Savage et al. |
| 6,059,766 A | 5/2000 | Greff |
| 6,077,257 A | 6/2000 | Edwards et al. |
| 6,141,577 A | 10/2000 | Rolland et al. |
| 6,146,378 A | 11/2000 | Mikus et al. |
| 6,146,380 A | 11/2000 | Racz et al. |
| 6,158,250 A | 12/2000 | Tibbals, Jr. et al. |
| 6,190,383 B1 | 2/2001 | Schmaltz et al. |
| 6,193,714 B1 | 2/2001 | McGaffigan et al. |
| 6,211,153 B1 | 4/2001 | Garnick et al. |
| 6,254,601 B1 | 7/2001 | Burbank et al. |
| 6,280,441 B1 | 8/2001 | Ryan |
| 6,296,639 B1 | 10/2001 | Truckai et al. |
| 6,306,097 B1 | 10/2001 | Park et al. |
| 6,306,129 B1 | 10/2001 | Little et al. |
| 6,315,741 B1 | 11/2001 | Martin et al. |
| 6,379,348 B1 | 4/2002 | Onik |
| 6,405,732 B1 | 6/2002 | Edwards et al. |
| 6,419,648 B1 | 7/2002 | Vitek et al. |
| 6,419,653 B2 | 7/2002 | Edwards et al. |
| 6,419,673 B1 | 7/2002 | Edwards et al. |
| 6,425,867 B1 | 7/2002 | Vaezy et al. |
| 6,432,067 B1 | 8/2002 | Martin et al. |
| 6,447,477 B2 | 9/2002 | Burney et al. |
| 6,463,331 B1 | 10/2002 | Edwards |
| 6,482,203 B2 | 11/2002 | Paddock et al. |
| 6,485,413 B1 | 11/2002 | Boppart et al. |
| 6,506,154 B1 | 1/2003 | Ezion et al. |
| 6,506,156 B1 | 1/2003 | Jones et al. |
| 6,506,171 B1 | 1/2003 | Vitek et al. |
| 6,507,747 B1 | 1/2003 | Gowda et al. |
| 6,508,815 B1 | 1/2003 | Strul et al. |
| 6,522,142 B1 | 2/2003 | Freundlich |
| 6,540,677 B1 | 4/2003 | Angelsen et al. |
| 6,543,272 B1 | 4/2003 | Vitek |
| 6,550,482 B1 | 4/2003 | Burbank et al. |
| 6,554,780 B1 | 4/2003 | Sampson et al. |
| 6,554,801 B1 | 4/2003 | Steward et al. |
| 6,559,644 B2 | 5/2003 | Froundlich et al. |
| 6,569,159 B1 | 5/2003 | Edwards et al. |
| 6,572,613 B1 | 6/2003 | Ellman et al. |
| 6,589,237 B2 | 7/2003 | Woloszko et al. |
| 6,592,559 B2 | 7/2003 | Pakter et al. |
| 6,602,251 B2 | 8/2003 | Burbank et al. |
| 6,610,054 B1 | 8/2003 | Edwards et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,623,481 B1 | 9/2003 | Garbagnati et al. |
| 6,626,854 B2 | 9/2003 | Friedman et al. |
| 6,626,855 B1 | 9/2003 | Weng et al. |
| 6,632,193 B1 | 10/2003 | Davison et al. |
| 6,635,055 B1 | 10/2003 | Cronin |
| 6,635,065 B2 | 10/2003 | Burbank et al. |
| 6,638,275 B1 | 10/2003 | McGaffigan |
| 6,638,286 B1 | 10/2003 | Burbank et al. |
| 6,645,162 B2 | 11/2003 | Friedman et al. |
| 6,645,202 B1 | 11/2003 | Pless et al. |
| 6,652,516 B1 | 11/2003 | Gough |
| 6,660,002 B1 | 12/2003 | Edwards et al. |
| 6,660,024 B1 | 12/2003 | Flaherty et al. |
| 6,663,624 B2 | 12/2003 | Edwards et al. |
| 6,663,626 B2 | 12/2003 | Truckai et al. |
| 6,666,833 B1 | 12/2003 | Friedman et al. |
| 6,669,643 B1 * | 12/2003 | Dubinsky ............... 600/459 |
| 6,679,855 B2 | 1/2004 | Horn et al. |
| 6,685,639 B1 | 2/2004 | Wang et al. |
| 6,689,128 B2 | 2/2004 | Sliwa, Jr. et al. |
| 6,692,490 B1 | 2/2004 | Edwards |
| 6,701,931 B2 | 3/2004 | Sliwa, Jr. et al. |
| 6,705,994 B2 | 3/2004 | Vortman et al. |
| 6,712,815 B2 | 3/2004 | Sampson et al. |
| 6,716,184 B2 | 4/2004 | Vaezy et al. |
| 6,719,755 B2 | 4/2004 | Sliwa, Jr. et al. |
| 6,728,571 B1 | 4/2004 | Barbato |
| 6,730,081 B1 | 5/2004 | Desai |
| 6,735,461 B2 | 5/2004 | Vitek et al. |
| 6,743,184 B2 | 6/2004 | Sampson et al. |
| 6,746,447 B2 | 6/2004 | Davison et al. |
| 6,764,488 B1 | 7/2004 | Burbank et al. |
| 6,773,431 B2 | 8/2004 | Eggers et al. |
| 6,790,180 B2 | 9/2004 | Vitek |
| 6,805,128 B1 | 10/2004 | Pless et al. |
| 6,805,129 B1 | 10/2004 | Pless et al. |
| 6,813,520 B2 | 11/2004 | Truckai et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,840,935 B2 | 1/2005 | Lee |
| 6,936,048 B2 | 8/2005 | Hurst |
| 6,994,706 B2 | 2/2006 | Chornenky et al. |
| 7,517,346 B2 | 4/2009 | Sloan et al. |
| 2001/0014805 A1 | 8/2001 | Burbank et al. |
| 2001/0051802 A1 | 12/2001 | Woloszko et al. |
| 2002/0002393 A1 | 1/2002 | Mitchell |
| 2002/0022835 A1 | 2/2002 | Lee |
| 2002/0052600 A1 | 5/2002 | Davison et al. |
| 2002/0068871 A1 | 6/2002 | Mendlein et al. |
| 2002/0077550 A1 | 6/2002 | Rabiner et al. |
| 2002/0183735 A1 | 12/2002 | Edwards et al. |
| 2003/0009164 A1 | 1/2003 | Woloszko et al. |
| 2003/0014046 A1 | 1/2003 | Edwards |
| 2003/0028111 A1 | 2/2003 | Vaezy et al. |
| 2003/0114732 A1 | 6/2003 | Webler et al. |
| 2003/0130575 A1 | 7/2003 | Desai et al. |
| 2003/0130655 A1 | 7/2003 | Woloszko et al. |
| 2003/0195420 A1 | 10/2003 | Mendlein et al. |
| 2003/0199472 A1 | 10/2003 | Al-Hendy et al. |
| 2003/0216725 A1 | 11/2003 | Woloszko et al. |
| 2003/0216759 A1 | 11/2003 | Burbank et al. |
| 2004/0002699 A1 | 1/2004 | Ryan et al. |
| 2004/0006336 A1 | 1/2004 | Swanson |
| 2004/0030268 A1 | 2/2004 | Weng et al. |
| 2004/0054366 A1 | 3/2004 | Davison et al. |
| 2004/0120668 A1 | 6/2004 | Loeb |
| 2004/0143252 A1 | 7/2004 | Hurst |
| 2004/0153057 A1 | 8/2004 | Davison |
| 2004/0175399 A1 | 9/2004 | Schiffman |
| 2004/0176760 A1 | 9/2004 | Qiu |
| 2004/0193028 A1 | 9/2004 | Jones et al. |

(56) References Cited

U.S. PATENT DOCUMENTS

| | | |
|---|---|---|
| 2004/0215182 A1 | 10/2004 | Lee |
| 2004/0230190 A1 | 11/2004 | Dahla et al. |
| 2004/0254572 A1 | 12/2004 | McIntyre et al. |
| 2005/0038340 A1 | 2/2005 | Vaezy et al. |
| 2005/0096647 A1* | 5/2005 | Steinke et al. .................. 606/41 |
| 2005/0107781 A1 | 5/2005 | Ostrovsky et al. |
| 2005/0124882 A1 | 6/2005 | Ladabaum et al. |
| 2005/0149013 A1 | 7/2005 | Lee |
| 2005/0177209 A1 | 8/2005 | Leung et al. |
| 2005/0197577 A1 | 9/2005 | Makin et al. |
| 2005/0215990 A1 | 9/2005 | Govari |
| 2005/0228288 A1 | 10/2005 | Hurst |
| 2005/0255039 A1 | 11/2005 | Desai |
| 2005/0256405 A1 | 11/2005 | Makin et al. |
| 2006/0010207 A1 | 1/2006 | Akerman et al. |
| 2006/0178665 A1 | 8/2006 | Sloan |
| 2006/0189972 A1 | 8/2006 | Grossman |
| 2007/0006215 A1 | 1/2007 | Epstein et al. |

FOREIGN PATENT DOCUMENTS

| | | |
|---|---|---|
| WO | WO 98/14169 | 4/1998 |
| WO | WO 99/43366 | 9/1999 |
| WO | WO 00/00098 | 1/2000 |
| WO | WO 01/80723 A2 | 11/2001 |
| WO | WO 01/95819 A1 | 12/2001 |
| WO | WO 02/11639 A1 | 2/2002 |
| WO | WO 03/005882 A2 | 1/2003 |
| WO | WO 03/005882 A3 | 1/2003 |
| WO | WO 03/065908 A1 | 8/2003 |
| WO | WO 2004/002293 A2 | 1/2004 |
| WO | WO 2004/002550 A2 | 1/2004 |
| WO | WO 2004/020011 A1 | 3/2004 |
| WO | WO 2004/035110 A2 | 4/2004 |
| WO | WO 2004/058328 A2 | 7/2004 |
| WO | WO 2004/064658 | 8/2004 |

OTHER PUBLICATIONS

Supplementary European Search Report and Search Opinion of EP Application No. 07797073, dated Oct. 29, 2009, 6 pages total.

Alterovitz et al., "Simulating Needle Insertion and Radioactive Seed Implantation for Prostate Brachytherapy," *Medicine Meets Virtual Reality* 11, Westwood et al. (Eds.), IOS Press, Jan. 2003, pp. 19-25.

Bergamini et al., "Laparoscopic Radiofrequency Thermal Ablation: A New Approach to Symptomatic Uterine Myomas," *Am. J. Obstetrics and Gynecology* (2005) 192: 768-73.

CNN.com Health Women, "Experimental technique uses lasers to shrink uterine fibroids," Nov. 28, 2000.

Hindley et al.; "MRI guidance of focused ultrasound therapy of uterine fibroids: Early results," *American Journal of Roentgenology*, 2004, 183(6): 1173-1719.

Kanaoka et al., "Microwave endometrial ablation at a frequency of 2.45 Ghz. A pilot study," *J Reprod Med.* Jun. 2001; 46(60): 559-63.

Law et al., "Magnetic resonance-guided percutaneous laser ablation of uterine fibroids," *J Magn Reson Imaging*, Oct. 2000; 12(4):565-70.

Liu et al., "Catheter-Based Intraluminal Sonography," *J. Ultrasound Med.*, 2004, 23:145-160.

Mogami et al., "Usefulness of MR-guided percutaneous cryotherapy," *Med. Imaging Technol.* 2004, 22(3): 131-6. (English abstract).

MSNBC OnLine Articles, About Us: Articles; "Intrauerine Fibroids Can Now Be Treated Nonsurgically".

Okamura et al., "Force Modeling for Needle Insertion into Soft Tissue," *IEEE Transactions on Biomedical Engineering*, Oct. 2001, 10 (51): 1707-1716.

RSNA 2000 Explore News Release; "Lasers Liquefy Uterine Fibroid Tumors," 11:30 a.m. CST, Monday, Nov. 27, 2000

Senoh et al., "Saline Infusion Contrast Intrauterine Sonographic Assessment of the Endometrium with High-Frequency, Real-Time Miniature Transducer Normal Menstrual Cycle: a Preliminary Report," *Human Reproduction*, 14 (10): 2600-2603, 1999.

Websand, Inc., *New treatment options for fibroid tumors*, Copyright 2002 by WebSand, Inc.

* cited by examiner

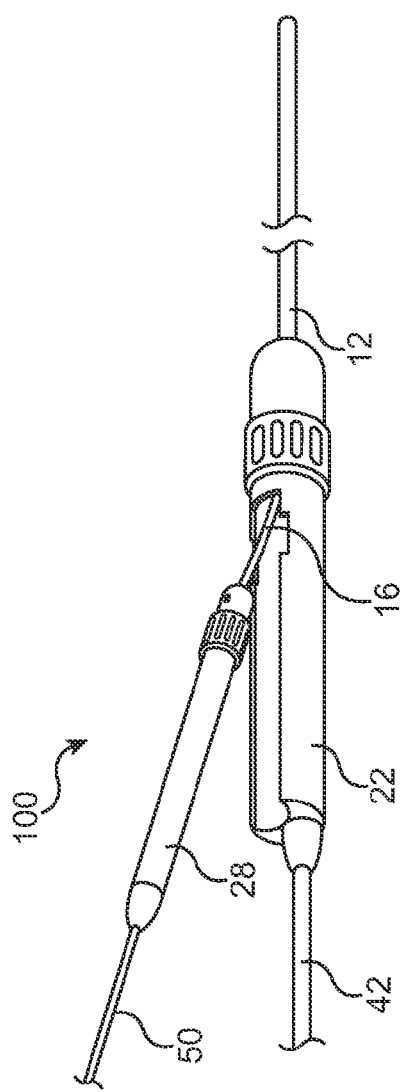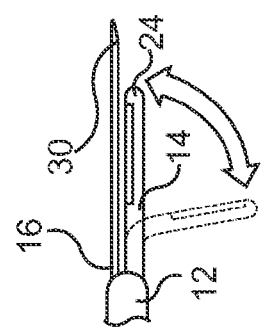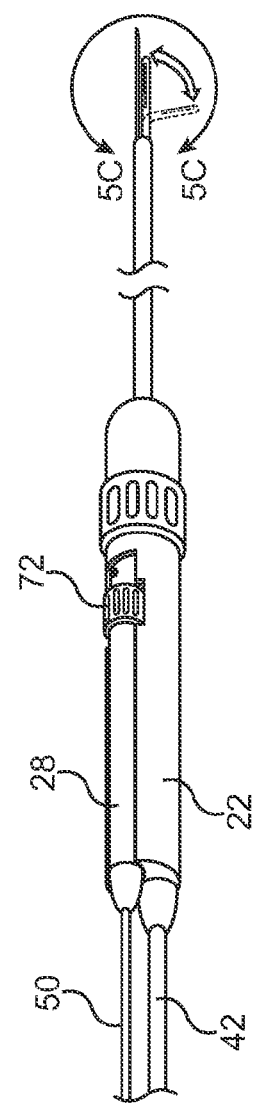

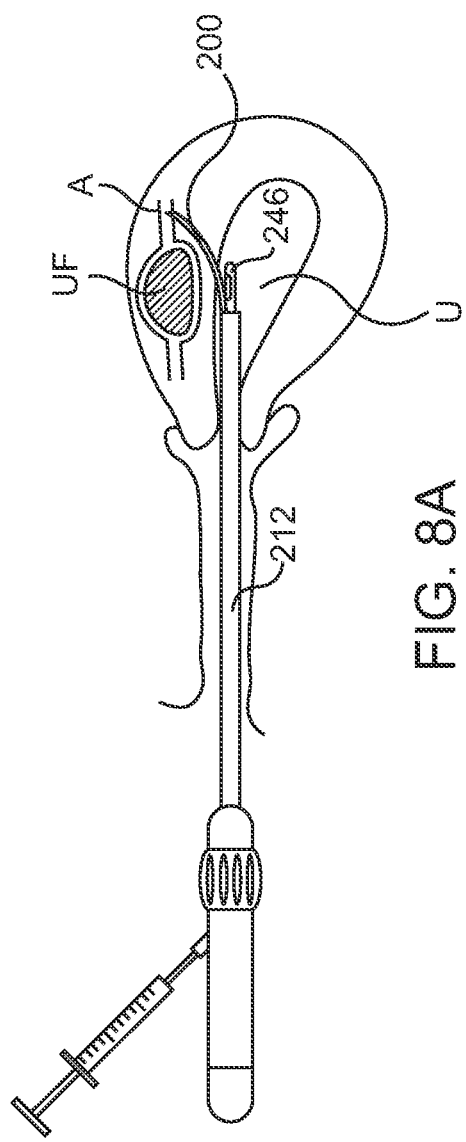
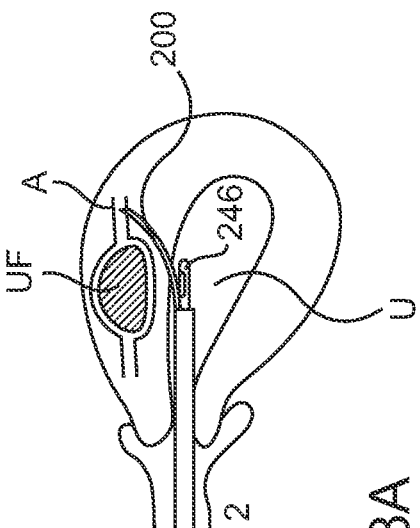
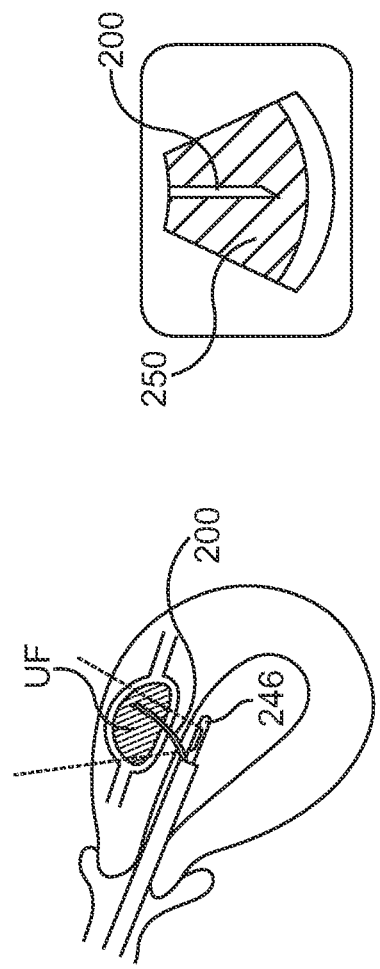
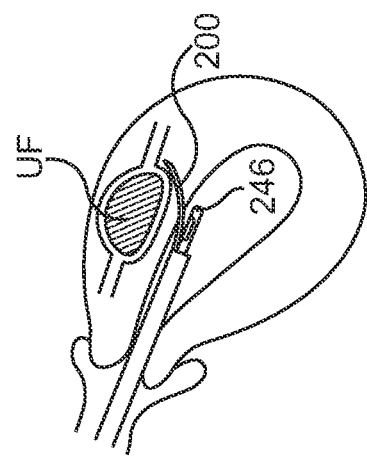
FIG. 8A
FIG. 8B
FIG. 8C
FIG. 9

INTERVENTIONAL DEPLOYMENT AND IMAGING SYSTEM

CROSS-REFERENCES TO RELATED APPLICATIONS

The present application claims the benefit of provisional U.S. application Ser. No. 60/758,881, filed Jan. 12, 2006, the full disclosure of which is incorporated herein by reference.

BACKGROUND OF THE INVENTION

Field of the Invention

The present invention relates generally to medical devices and methods. More particularly, the invention relates to systems which provide for removably positioning an imaging core and an interventional core in a sheath and to methods for using such systems.

Treatment of the female reproductive tract for dysfunctional uterine bleeding and fibroids remain unmet clinical needs. Fibroids are benign tumors of the uterine myometria (muscle) and are the most common tumor of the female pelvis. Fibroid tumors affect up to 30% of women of childbearing age and can cause significant symptoms such as discomfort, pelvic pain, menorrhagia (excessive menstrual bleeding), pressure, anemia, compression, infertility and miscarriage. Fibroids may be located in the myometrium (intramural), adjacent to the endometrium (submucosal) or in the outer layer of the uterus (subserosal). Most commonly fibroids are a smooth muscle overgrowth that arise intramurally and can grow to be several centimeters in diameter.

Current treatments for fibroids include both pharmacological therapies and surgical interventions. Pharmacological treatment includes the administration of medications such as NSAIDS, estrogen-progesterone combinations, and GnRH analogues. All medications are relatively ineffective and are palliative rather than curative. Hysterectomy (surgical removal of the uterus) is another common treatment for fibroids. While effective, hysterectomy has many undesirable side effects such as loss of fertility, the need for open surgery, sexual dysfunction, and long recovery time. There is also significant morbidity (sepsis, hemorrhage, peritonitis, bowel and bladder injury), mortality and cost associated with hysterectomy. Surgical myomectomy, in which fibroids are removed, is an open surgical procedure requiring laparotomy and general anesthesia. Often these procedures result in significant blood loss and remove a portion of the fibroid mass.

To overcome at least some of the problems associated with open surgical procedures, laparoscopic myomectomy was pioneered in the early 1990's. However, laparoscopic myomectomy remains technically challenging, requiring laparoscopic suturing which limits its performance to only the most skilled of laparoscopic gynecologists. Other minimally invasive treatments for uterine fibroids include hysteroscopy, uterine artery ablation, endometrial ablation, and myolysis.

Hysteroscopy utilizes a thin fiber optic camera to image the uterus and an attachment to destroy tissue. Hysteroscopic resection is a surgical technique that uses a variety of devices (loops, roller balls, bipolar electrodes) to ablate or resect uterine tissue. The uterus needs to be filled with fluid for better viewing and thus has potential side effects of fluid overload. Hysteroscopic ablation is limited by its visualization technique and is thus only appropriate for those fibroids that are submucosal and/or protrude into the uterine cavity.

Uterine artery embolization was introduced in the early 1990's and is performed through a groin incision by injecting small particles into the uterine artery to selectively block the blood supply to fibroids. Complications include pelvic infection, premature menopause and severe pelvic pain. In addition, long term MRI data suggest that incomplete fibroid infarction may result in regrowth of infarcted fibroid tissue and symptomatic recurrence.

Endometrial ablation is primarily a procedure for dysfunctional (or abnormal) uterine bleeding and may be used at times for fibroids. Endometrial ablation relies on various energy sources such as cryo energy, microwave energy and radiofrequency energy. Endometrial ablation destroys the endometrial tissue lining the uterus but does not specifically treat fibroids. This technique is also not for women who desire future childbearing. Endometrial ablation remains an excellent therapy for dysfunctional uterine bleeding but is limited in its ability to treat fibroids.

Myolysis was first performed in the 1980's using lasers or RF energy to coagulate tissue, denature proteins and necrose myometrium with laparoscopic visualization. Laparoscopic myolysis can be an alternative to myomectomy, as the fibroids are coagulated and then undergo coagulative necrosis resulting in a dramatic decrease in size. As with all laparoscopic techniques, myolysis is limited by the fact that it can only see (and therefore treat) subserosal fibroids.

Needle myolysis uses a laparoscope to introduce one or more needles into a fibroid tumor under visual control. Bipolar Radio Frequency ("RF") current is then delivered between two adjacent needles, or unipolar current between a single needle and a distant dispersive electrode affixed to the thigh or back. The aim of needle myolysis is to coagulate a significant volume of the tumor and thereby cause it to shrink substantially. The traditional technique is to make multiple passes through different areas of the tumor using the coagulating needle to destroy many cylindrical cores of abnormal tissue. However, the desirability of multiple passes is mitigated by the risk of adhesion formation, which is thought to increase with increasing amounts of injured uterine serosa, and by the operative time and skill required.

To overcome the limitations of current techniques, it would be desirable to provide a minimally invasive approach to selectively eradicate fibroid tumors within the uterus. It would be particularly desirable to provide a treatment device that combines imaging and ablation in one simple hand held unit or assembly. It would be further desirable if the method and apparatus could locate and treat all types of fibroids in the uterus in a safe and effective manner with minimum risk and discomfort for the patient. It would be still further desirable if the devices could employ multiple interchangeable components both to permit selective sterilization or reuse of the devices and to permit the system to be configured individually for patients having different anatomies and needs. It would be still further desirable if such devices could be used in and for procedures used in other parts of the anatomy in addition to the uterus. At least some of the objectives will be met by the inventions described below.

BRIEF SUMMARY OF THE INVENTION

The present invention provides a needle deployment and imaging system which allows for needle deployment into solid tissue under direct, usually real-time, visualization. Typically, the needle will be deployed from within a natural or created body cavity or body lumen. Exemplary body cavities include the uterus, the esophagus, the stomach, the bladder, the colon, and the like. Exemplary body lumens include the ureter, the urethra, fallopian tubes, and the like. Created body cavities include insufflated regions in the abdomen, the thoracic cavity, regions around joints (for arthroscopic procedures), and the like. The present invention will generally not find use with procedures in blood vessels or other regions of the vasculature. Thus, while the following description will be directed particularly at procedures within the uterus for detecting and treating uterine fibroids, the scope of the present invention is not intended to be so limited.

Needle deployment and imaging systems according to the present invention will comprise a sheath, an imaging core, and an interventional core. The sheath will have a proximal end, a distal end, a first axial passage, and a second axial passage which is preferably isolated from the first axial passage. By "isolated" it is meant that the passages are separated by an internal wall or barrier that prevents cross-contamination from one passage to the other. The axial passages will typically extend the entire length of the sheath from the proximal to distal end and may be open at least the proximal end(s), often at both ends. In some instances, however, the passage(s) may be shorter and/or may be plugged or otherwise sealed at one end (usually the distal end) to isolate that end of the passage from the external environment. The sheath will usually be flexible, sometimes being deflectable or steerable, but in other instances may be rigid along all or a portion of its length. In some instances, at least a portion of the sheath at or near the distal end will be open or visually transparent to permit imaging from within the second axial passage. For example, at least a portion of the sheath may be composed of an ultrasonically translucent material to permit ultrasonic or optical coherence tomographic (OCT) imaging through a wall of the sheath. In other instances, the second axial passage may be open (e.g., provided with an open port or aperture) at its distal end to permit the imaging core to be advanced beyond the distal end of the sheath. Typically, the second axial or passage will be open at its distal end to permit advancement of a needle or other interventional element therethrough. In other instances, however, the second axial passage may be closed or covered by a penetrable septum or cover.

The imaging core may be adapted for any conventional form of medical imaging, such as ultrasonic imaging, optical coherence tomographic imaging (OCT), direct optic visualization (e.g., using optical fibers for image transmission or using in situ charged coupled devices (CCD's) or other imaging elements for in situ visualization), or the like. The imaging core will be disposed in the first axial passage, usually being removably disposed so that it may be removed and replaced within the sheath to permit sterilization and reuse of the imaging core. The imaging core will usually be flexible and in some instances may be deflectable or steerable, either in place of a steerable sheath or in addition to a steerable sheath.

The interventional core may be replaceably, translatably, or fixedly disposed in the second axial passage. In most cases, the interventional core will typically be advanceable or otherwise deployable from the sheath in order to effect the desired therapeutic or diagnostic procedure. In the specific embodiments described below, the interventional core will typically be a needle which is reciprocatably disposed within a second axial passage having an open distal end (and/or other lateral opening) to permit deployment and penetration into adjacent solid tissue. In those cases, the needle may be a radiofrequency (RF) electrode, a microwave antenna, a cryogenic probe, or other energy delivery or mediating element intended for ablating or otherwise treating the tissue. In other cases, the needle could be a hollow core needle intended for sampling, biopsy, or otherwise performing a diagnostic procedure, or for delivering a therapeutic agent or drug into the tissue.

In the most common embodiments, the imaging core will be removable and replaceable and the treatment core will be non-removably or at least non-replaceably coupled within the second passage (although being adapted for reciprocatable deployment is described above.) In such cases, the needle deployment and imaging system may be used for a therapeutic or diagnostic procedure and removed from the patient after the procedure is complete. The removable imaging core may then be removed and sterilized. The sheath and interventional core will then typically be disposed, although in other instances it's possible that they could be sterilized and reused.

In other embodiments, the imaging core may be fixed within the first axial passage while the interventional core is removable and replaceable within the sheath. In those instances, after the needle deployment and imaging system has been used in a procedure, the system will be extracted from the patient and the interventional core removed from the sheath. The removable interventional core will usually be sterilized for reuse, while the combination of the sheath and the imaging core will be disposed of or separately sterilized for reuse.

In still further embodiments, both the imaging core and the interventional core may be removable and replaceable within the respective axial passages of the sheath. After use of such needle deployment and imaging systems, both the imaging core and the interventional core may be removed from the respective axial passage. Each of the sheath, imaging core, and interventional core may then be disposed and/or sterilized for reuse as determined by the treating physician or medical facility at that time. Most commonly, at least the sheath would be disposed of, while either or both of the imaging core and the interventional core might be sterilized for reuse.

The geometries of the imaging core and the interventional core may be varied in accordance with the intended use of the needle deployment and imaging system. Usually, the imaging core will be adapted for lateral imaging and will be positionable within the first axial passage for side-viewing from the sheath. The first axial passage may be entirely sealed to the exterior with an ultrasonically, optically, or other visually transparent window formed in a wall of the sheath to permit imaging by the imaging core. The use of a sealed first axial passage is frequently preferred since it isolates the imaging core from the body cavity or lumen being treated or diagnosed. Alternatively, an open window could be formed within the wall of the sheath to permit imaging by the imaging core. Still further alternatively, the imaging core may be adapted to extend distally beyond an opening in the first axial passage at the distal end of the sheath to permit imaging. In such cases where the imaging core is distally extendable, at least a distal end of the imaging core will frequently be adapted for deflection or steering.

In still other embodiments of the present invention, the imaging core may be adapted to image in a distally forward direction. As with the lateral imaging embodiments, the sheath may be composed at least partially of an ultrasonically or otherwise visually transparent material and/or an opening may be formed in the sheath to permit imaging therethrough.

In the preferred case of ultrasonic imaging cores, the ultrasonic transducers may be arranged in a phased array, for example either a linear (typically axially aligned) phased array or a circumferential phased array. Alternatively the ultrasonic imaging element may comprise one or more independent elements, such as parabolic or other shaped imaging elements. In still further embodiments, the ultrasonic imaging transducers may be arranged in a rotating mechanism to permit rotational scanning.

A particular advantage of the present invention will be the ability to selectively position both the imaging core and the interventional core within the body cavity or lumen being treated or diagnosed. The positioning capabilities may come from the sheath, the imaging core, and/or less frequently from the interventional core. In some embodiments, the sheath will either be steerable or deflectable, often using single or multiple tensioning wires for selective deflection of the distal end. Alternatively, the sheath may be provides as a kit including a plurality of sheaths having different distal end geometries intended for particular anatomies and anatomical access routes. In such instances, the systems will comprise at least a first and second sheath, often including third, fourth, fifth, or additional sheaths, each having a unique distal end geometry.

In still other systems, the imaging core may itself be steerable or deflectable, again typically being provided by one or more pull or tensioning wires. Such steerable or deflectable imaging cores may be deployed or manipulated within the first axial passage of the sheath so that deflection of the core will in turn deflect a distal portion of the sheath. Alternatively or additionally, the imaging cores may be deployable beyond the distal end of the sheath so that the core may be deflected and reoriented outside the sheath. Such deployment and actuation of the steerable imaging cores will be particularly useful with sheaths having rigid, non-bendable structures, although they could also be used with sheaths having steering mechanisms.

The interventional cores will typically comprise a needle or other tissue-penetrating element. Typically, the interventional cores will have a tissue-penetrating element at or near their distal ends, such as a sharpened distal tip, an RF cutting element at the tip, a removable stylet having a sharpened tip, or the like. In any event, the distal end will usually be adapted so that it will self-penetrate into the tissue as it is advanced from the sheath. The direction of advancement will be coordinated with the imaging field of the imaging core so that the penetration of the interventional core into tissue can be viewed by the practitioner, usually in real time. In the exemplary embodiments, a therapeutic needle advanced from the sheath can be viewed as it enters the uterine wall to treat a uterine fibroid. Such tissue-penetrating elements may be adapted to reciprocate through a side port in the sheath to extend laterally or may be adapted to reciprocate through a distal port in the sheath to extend axially.

BRIEF DESCRIPTION OF THE DRAWINGS

FIGS. 5A-5C illustrate insertion of an imaging core into a sheath where both the imaging core and an interventional core extend axially from a distal end of the sheath.

FIGS. 8A-8C illustrate use of a needle deployment and imaging system for delivering occlusive elements to a uterine artery in accordance with the principles of the present invention.

FIG. 9 illustrates the image viewable with the system of FIGS. 8A-8C.

DETAILED DESCRIPTION OF THE INVENTION

Figures 1, 1A:
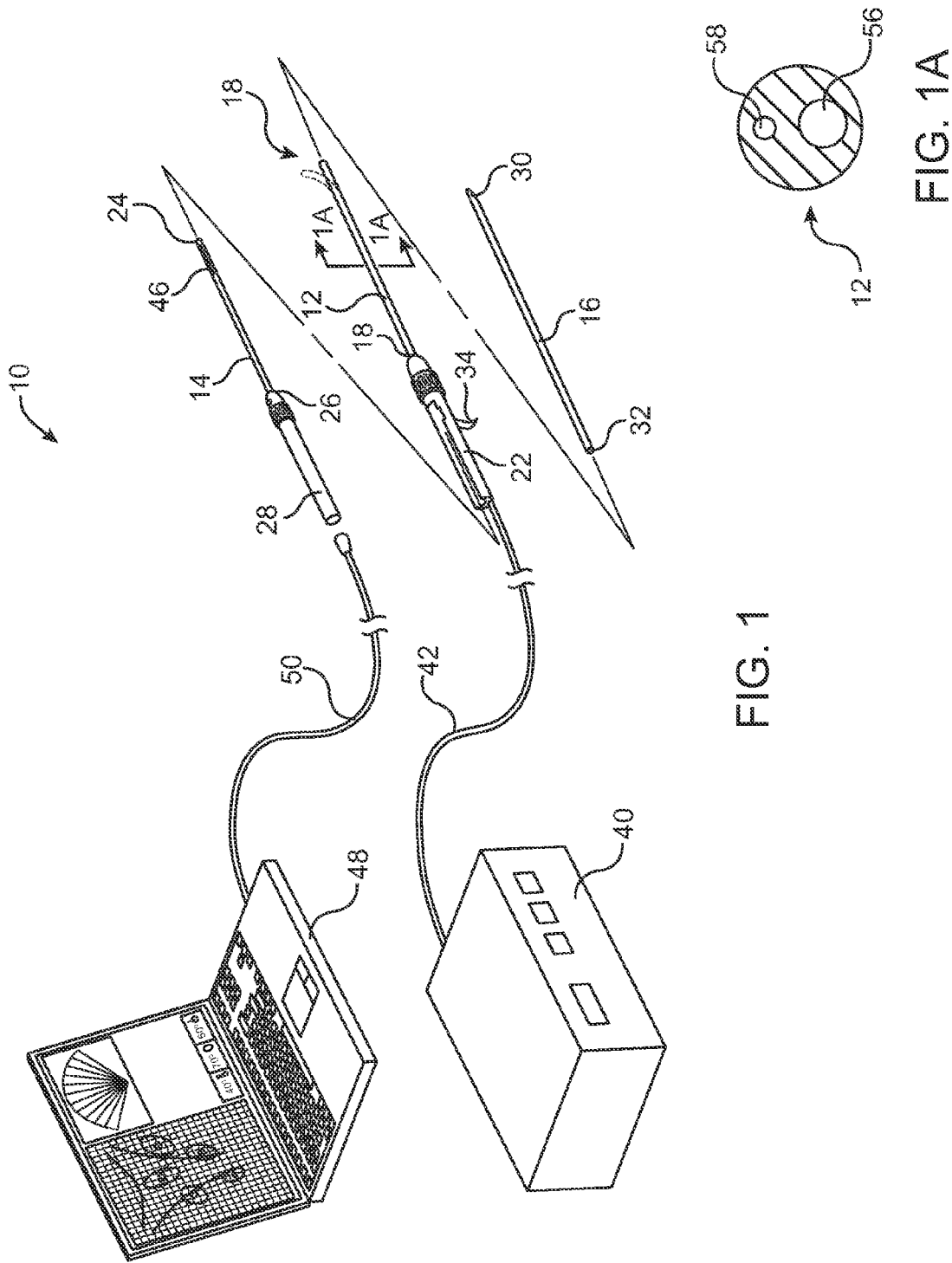
FIG. 1 is an exemplary illustration of a needle deployment and imaging device and system constructed in accordance with the principles of the present invention.
FIG. 1A is a cross-sectional view of the device taken along line 1A-1A in FIG. 1.

As seen in FIG. 1, a needle deployment and imaging system 10 comprises a sheath 12, an imaging core 14, and an interventional core 16. The sheath 12 has a distal end 18, a proximal end 20, and a handle structure 22 disposed at the proximal end. Imaging core 14 also has a distal end 24, a proximal end 26, and a handle structure 28 disposed at the proximal end. Similarly, the interventional core 16 has distal end 30, a proximal end 32, and will will usually have a trigger 34 or other deployment mechanism on the sheath 12 in order to axially reciprocate the needle from the proximal end 18 of the sheath.

As shown in FIG. 1, the interventional core 16 is a tissue-penetrating electrode where the distal end 30 is typically sharpened or otherwise adapted for penetrating or otherwise entering solid tissue when it is advanced from the sheath 12. The interventional core 16 will be connectable to an RF power supply 40 via a connecting cable 42 which attaches to the interventional core through the handle structure 22 of the sheath 12. A switch, foot pedal, or other trigger (not shown) is provided on or with the RF power supply 40 in order to initiate delivery of RF energy through the interventional core 16 in a generally conventional manner. The radiofrequency energy provided can be monopolar, bipolar, or combinations thereof as are well-known in the art of RF tissue ablation. In addition, the core 16 may have a lumen or other delivery means for saline infusion or "wet RF" as is well known to those skilled in the art.

The imaging core 14 typically comprises an ultrasonic imaging transducer or transducer array 46 near its distal end 24. The ultrasonic transducer or array 46 is connectable to an imaging monitor 48, illustrated in the form of a laptop computer, via a cable 50 attachable to the handle structure 28 of the imaging core 14. It will be appreciated that in other embodiments, the imaging monitor 48 could be combined with the RF power supply 40 in a single unit providing for both interventional control and image monitoring.

In the embodiment of FIG. 1, the imaging core 14 is removably placed in a first axial passage 56 extending through the sheath 12, as shown in FIG. 1A. The interventional core 16 is to be disposed within a second axial passage 58 which is usually formed in parallel in the sheath body 12, as also shown in FIG. 1A. In the embodiment of FIG. 1, the interventional core 16 will be reciprocatable within the second axial passage 58 to extend either axially or laterally from the distal end of the sheath 12. Usually, the proximal end of the interventional core 16 will be non-removeably coupled to the trigger 34 or other advancement component of the sheath so that the interventional core is not intended to be removable and replaceable.

Figure 2A:
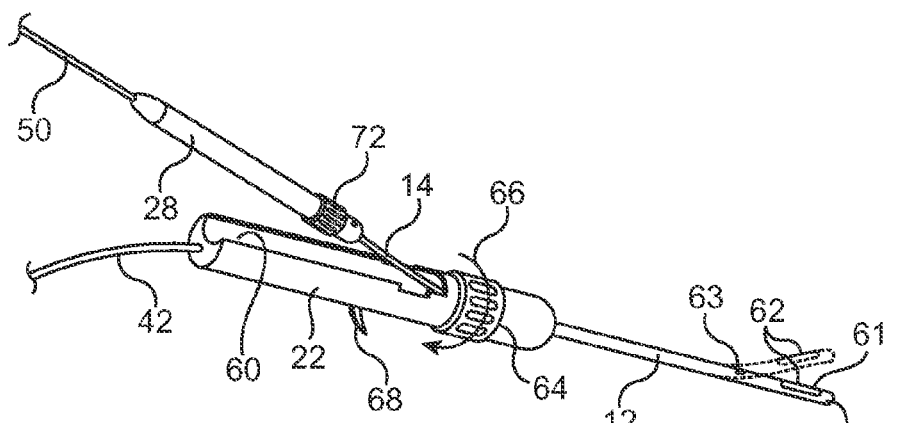
FIGS. 2A and 2B illustrate insertion of a first embodiment of steerable imaging core into a sheath in accordance with the principles of the present invention.
Figure 2B:
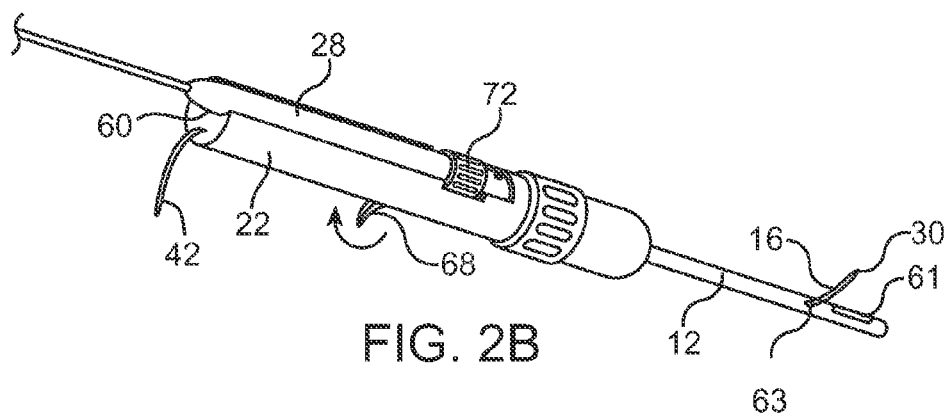

Referring now to FIGS. 2A and 2B, the imaging core 14 is loaded into the first axial passage 56 of the sheath 12 by advancing the core through a cradle 60 formed in the handle structure 22. When fully inserted, the handle structure 28 is fully received into cradle 60, as shown in FIG. 2B. In this embodiment, the first axial passage 60 is sealed over its entire length within the sheath 12 and an acoustically transparent window 62 is formed near the distal end 18 of the sheath. The distal end 18 of the sheath 12 may be deflected by rotating a control knob 64 on the handle structure 22, as shown by arrow 66 in FIG. 2A. In other embodiments, the sheath 12 will be rigid and non-steerable. The distal end 30 of the interventional core 16 may be advanced from the distal end 18 of the sheath by pulling a trigger 68 on the handle structure 22 of the sheath 12, as shown in FIG. 2B. The distal end 24 of the imaging core 14 is optionally deflectable using a control knob 72 on the handle structure 28, although deflection of the imaging core is not illustrated in the figures.

Figure 3:
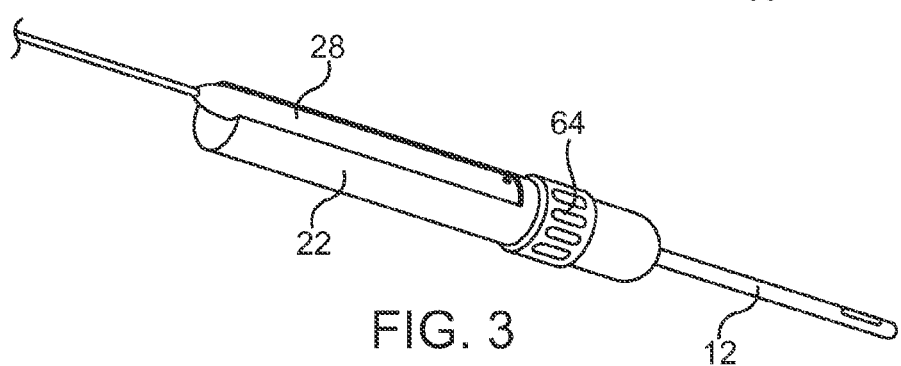
FIG. 3 illustrates an alternative embodiment of a non-steerable imaging core within a sheath in accordance with the principles of the present invention.
Figure 4:
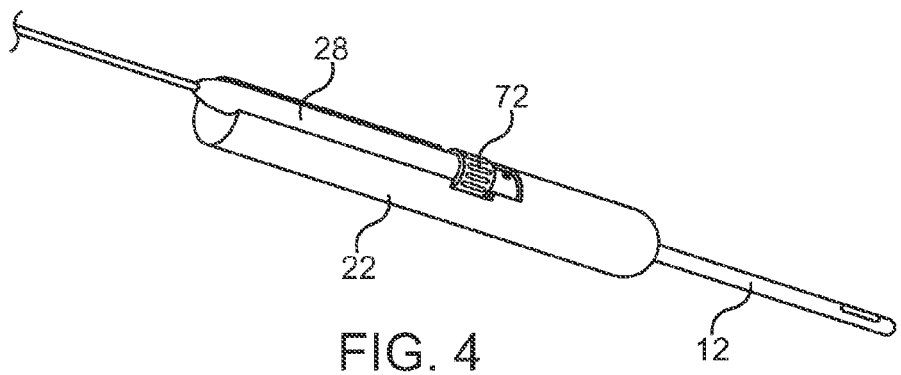
FIG. 4 illustrates a still further embodiment of a non-steerable imaging core within a non-steerable sheath in accordance with the principles of the present invention.

While it will often be desirable to provide deflection or steering capability in at least one of the sheath 12 and imaging core 14, it will not be necessary to provide such steering in either or both the sheath and imaging core as shown in the embodiment of FIG. 1. For example, as shown in FIG. 3, the handle structure 22 may have the control knob 64 for deflecting the distal end of sheath 12, while the handle structure 28 may be free of control knobs and the imaging core 14 may not be steerable. Alternatively, the sheath 12 may be non-steerable, with the imaging core 14 being steerable, as shown in FIG. 4. In still other embodiments, neither the sheath nor the imaging core may be steerable, e.g., when the sheath has a permanently deflected distal end or is provided as a kit including multiple sheaths, as illustrated in FIG. 6A-6D, and described in detail below.

Deployment of the imaging core 14 and interventional core 16 from and/or within the sheath 12 may be accomplished in a variety of ways. In the embodiment of FIG. 1, 2A, and 2B, the first passage 56 is sealed (typically with an acoustically transparent window 61 so that the imaging core 14 remains within the passage and is never extended from the sheath. The interventional core 16, in contrast, is extended through a port 63 in the side of the sheath 12 in a lateral direction, as best shown in FIG. 2B.

Referring now to FIGS. 5A and 5B, an embodiment 100 of the needle deployment and imaging system of the present invention includes sheath 12, imaging core 14, and interventional core 16 which are generally the same as described previously with reference to FIGS. 1, 2A and 2B, except for the distal end deployment configurations. As shown in FIG. 5A, imaging core 14 is loaded into the sheath 12 as described above, and the only significant difference with the prior embodiment is that the sheath 12 does not necessarily include an acoustically or optically transparent window at its distal end. Instead as best shown in FIG. 5B, both the distal end 30 of the interventional core 16 and the distal end 24 of the imaging core 14 are extendable through ports in the distal end of the sheath 12. Moreover, the distal end 24 of the imaging core 14 is deflectable using the control knob 72 of the handle structure 28, as shown in broken line. The distal end of the sheath 12 will also be steerable, and the embodiment of the needle deployment and imaging system 100 will allow access to a variety of tissue surfaces within the uterine or other body cavities by steering of the sheath, deflection of the imaging core, and rotation of the imaging core relative to the sheath.

Figure 6A:
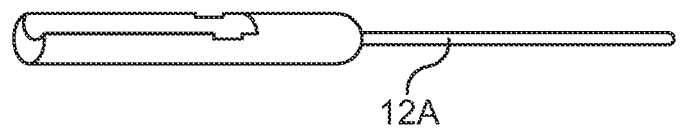
FIGS. 6A-6D illustrate sheaths having pre-shaped distal ends intended for intrauterine treatments.
Figure 6B:
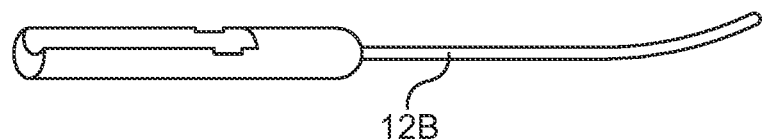
Figure 6C:
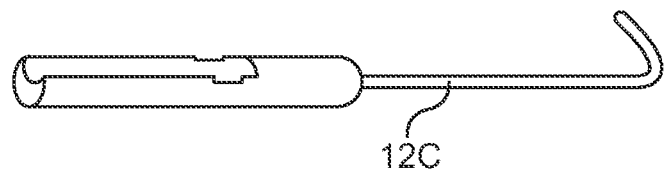
Figure 6D:
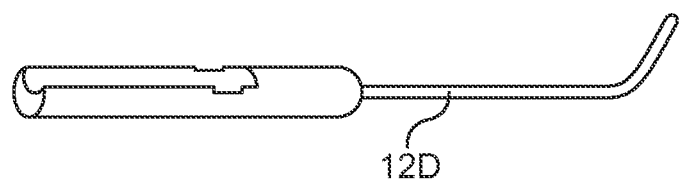

Referring now to FIGS. 6A-6D, a sheath kit will comprise a plurality of individual sheaths 12A, 12B, 12C, and 12D, and optionally still further sheaths. The distal end of each sheath 12A-12D will have a different shape which is permanently set into the sheath. While the sheath bodies may still retain a certain degree of flexibility, they will have sufficient rigidity in order to retain the pre-set shape. The simplest shape will be generally linear, as shown in FIG. 6A. The sheath 12B of FIG. 6B will have a gentle curve to facilitate access to the front and back of the uterus. The distal tip of the sheath 12C as illustrated in FIG. 6C will have a generally L-shaped deflection which permits access to the sidewalls of the uterus. Finally, the sheath 12D of FIG. 6D will have a curve intermediate those of sheaths 12B and 12C to allow access to the fundus of the uterus. Still further geometries may be useful for access and interventions within the uterus and other body cavities and lumens.

Figure 7A:
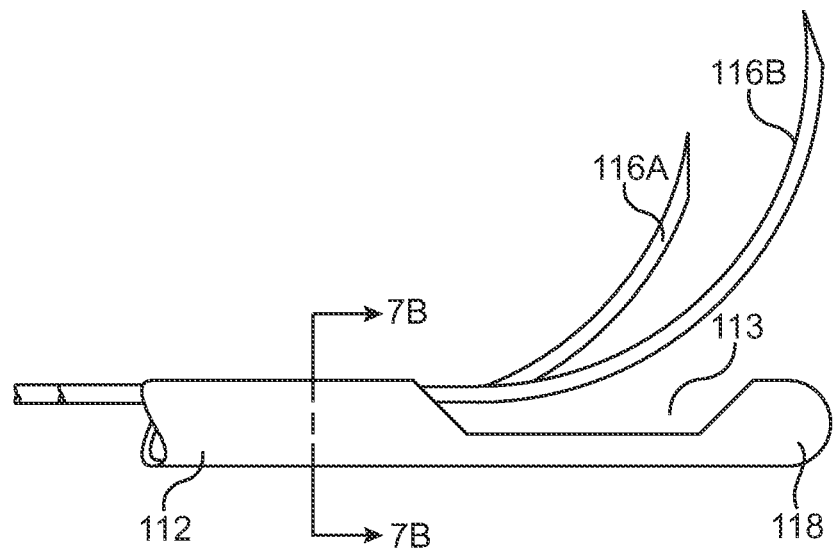
FIGS. 7A and 7B illustrate a still further embodiment of a sheath having an open window near its distal end for deployment of a pair of needle-type interventional cores.
Figure 7B:
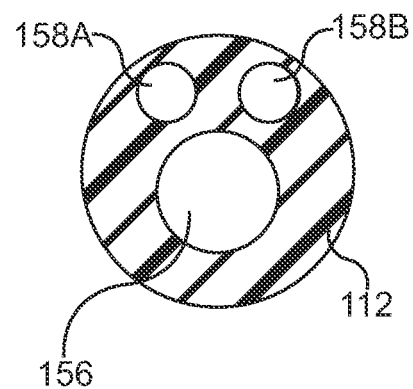

Referring now to FIGS. 7A and 7B, it will be appreciated that a wide variety of needle geometries and sheath configurations may be utilized. For example, a sheath 112 may have a Notch-like opening 113 near its distal end 118 to permit one or more tissue-penetrating needles 116A and 116B to be advanced forwardly and laterally relative to the access of the sheath, as shown in FIG. 7A. The needles 116A and 116B will be reciprocatably received within axial passages 158A and 158B through the sheath 112, as best shown in FIG. 7B. An additional axial passage 156 will be provided for an imaging core (not shown) which will be advanced through the sheath 112 and be positioned within the open notch 113 for imaging of the needles 116A and 116B as they are being deployed in solid tissue.

Referring now to FIGS. 8A-8C and FIG. 9, the needle deployment and imaging systems of the present invention can be used for delivering substances, energy, or a variety of other interventional modes to treat uterine fibroids UF in the wall of the uterus U. As shown in FIG. 8A, a hollow delivery needle 200 may be advanced from the distal end of the sheath 212 under ultrasonic imaging provided by an array 246. The needle 200 may be deployed in an artery A supplying blood to the uterine fibroid F, and occlusive elements delivered to the artery in order to occlude the artery to deprive the fibroid of blood.

As shown in FIGS. 8B and 8C, the needles 200 could also be configured to enter into tissue adjacent the fibroid UF as shown in FIG. 8B, or within the fibroid UF as shown in FIG. 8C. A variety of materials, such as markers, dyes, fluid blebs, air blebs, solid materials, biodegradable materials, and the like, could also be delivered using these needles in any of the illustrated configurations. As shown in FIG. 9, the location of the needle 200 within the field of view 250 can be observed in real time using the ultrasonic imaging array 246.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A needle deployment and imaging system comprising:
   a sheath having a proximal end, a distal end, and a handle structure at the proximal end, wherein the sheath is open at its proximal end and at its distal end;
   an imaging core removably coupled to the sheath and adapted to be inserted into the sheath through the open proximal end, removed from the sheath through the open proximal end, and reused, wherein an imaging transducer on the core extends through the open distal end of the sheath when the core is present therein and wherein the imaging transducer may be deflected when the transducer extends beyond the sheath, and wherein the imaging core further comprises a handle structure at a proximal end of the imaging core, the handle structure of the sheath being configured to mate with the handle structure of the imaging core; and
   an interventional core disposed in the sheath.

2. A system as in claim 1, wherein the interventional core is non-removably disposed in the sheath.

3. A system as in claim 1, wherein the imaging core is adapted to image in a lateral direction.

4. A system as in claim 1, wherein the imaging core comprises an ultrasonic transducer adapted for imaging.

5. A system as in claim 4, wherein the ultrasonic transducer comprises a phased array of transducer elements.

6. A system as in claim 1, wherein the imaging core has a distal end which is selectively deflectable.

7. A system as in claim 6, wherein the imaging core comprises at least one pull wire to effect deflection.

8. A system as in claim 1, wherein the interventional core comprises a tissue-penetrating element which is axially reciprocatable relative to the sheath.

9. A system as in claim 8, wherein the tissue-penetrating element is adapted to reciprocate through a distal port to extend axially from the sheath.

10. A system as in claim 8, wherein the tissue-penetrating element comprises an electrode adapted to deliver electrical current to tissue.

11. A system as in claim 8, wherein the tissue-penetrating element is a hollow needle adapted to deliver substances to tissue or associated vasculature.

12. A system as in claim 1, wherein when the handle structures of the imaging core and the sheath are mated, the imaging core and the interventional core are in a predetermined geometric relationship with one another.

13. A system as in claim 1, wherein the handle structure of the sheath comprises a cradle adapted to receive the handle structure of the core when the imaging core and the sheath are mated.

14. A system for treating uterine fibroids, said system comprising:
    a sheath having a proximal end, a distal end, and a handle structure at the proximal end, wherein the sheath is open at its proximal end and at its distal end and the sheath is adapted to be transvaginally introduced to locate the distal end in a uterus;
    an ultrasonic imaging core removably coupled to the sheath and having a field of view, said imaging core adapted to be inserted into the sheath through the open proximal end, removed from the sheath through the open proximal end, and sterilized for reuse, wherein an imaging transducer on the core extends through the open distal end of the sheath when the core is present therein and wherein the imaging transducer may be deflected when the transducer extends beyond the sheath, and wherein the imaging core further comprises a handle structure at a proximal end of the imaging core, the handle structure of the sheath being configured to mate with the handle structure of the imaging core; and
    a needle reciprocatably positioned in the sheath and having a distal end which is positionable in the field of view of the ultrasonic imaging core.

15. A system as in claim 14, wherein the needle reciprocates axially.

16. A system as in claim 14, wherein the ultrasonic imaging core is adapted to image laterally.

17. A system as in claim 16, wherein the needle reciprocates laterally.

18. A system as in claim 14, wherein the needle comprises an electrode adapted to deliver electrical current to tissue.

19. A system as in claim 14, wherein the needle is a hollow needle adapted to deliver substances to tissue or associated vasculature.

20. A system as in claim 14, wherein the ultrasonic imaging core comprises a phased array transducer.

21. A system as in claim 14, wherein the ultrasonic imaging core is flexible over at least its distal end.

22. A system as in claim 14, wherein the ultrasonic imaging core has a distal end which is selectively deflectable.

23. A system as in claim 22, wherein the ultrasonic imaging core comprises at least one pull wire to effect deflection.

24. A system as in claim 14, wherein when the handle structures of the imaging core and the sheath are mated, the imaging core and the needle are in a predetermined geometric relationship with one another.

25. A system as in claim 14, wherein the handle structure of the sheath comprises a cradle adapted to receive the handle structure of the core when the imaging core and the sheath are mated.

* * * * *